United States Patent

Andes et al.

[11] Patent Number: 5,460,041
[45] Date of Patent: Oct. 24, 1995

[54] APPARATUS AND METHOD FOR CONTINUOUS MEASUREMENT OF THE WET BULB TEMPERATURE OF A FLUE GAS STREAM

[75] Inventors: Gary M. Andes; Richard Marshall, both of Lockport, N.Y.; Andrew D. Burnette, Austin, Tex.; Lawrence R. Lepovitz, Paducah, Ky.

[73] Assignee: Electric Power Research Institute, Inc., Palo Alto, Calif.

[21] Appl. No.: 394,564

[22] Filed: Feb. 27, 1995

Related U.S. Application Data

[63] Continuation of Ser. No. 148,299, Nov. 8, 1993, abandoned.

[51] Int. Cl.[6] ........................................ G01N 25/64
[52] U.S. Cl. ........................................ 73/335.08; 374/148
[58] Field of Search .................. 73/25.04, 29.01, 73/29.02, 335.06, 335.08, 29.05; 374/28, 141, 148

[56] References Cited

U.S. PATENT DOCUMENTS

| | | | |
|---|---|---|---|
| 1,329,112 | 1/1920 | Cramer et al. | 73/335.06 |
| 1,635,697 | 7/1927 | Amdursky | 73/335.08 |
| 1,690,155 | 11/1928 | Amdursky | 73/335.06 |
| 3,253,465 | 5/1966 | Miller | 73/335.08 |
| 4,129,250 | 12/1978 | Chaikin et al. | 236/44 A |
| 4,222,261 | 9/1980 | Leblanc et al. | 73/335.08 |
| 4,809,537 | 3/1989 | Glover et al. | 73/29 |
| 4,836,991 | 6/1989 | Ishiguro et al. | 423/242 |
| 4,890,479 | 1/1990 | Glover et al. | 73/29 |
| 5,016,472 | 5/1991 | Amrhein et al. | 73/338 |
| 5,040,417 | 8/1991 | Rowlette | 73/336.5 |

*Primary Examiner*—Hezron E. Williams
*Assistant Examiner*—Michael J. Brock
*Attorney, Agent, or Firm*—James W. Maccoun

[57] ABSTRACT

In a flue gas scrubber for removing sulfur dioxide from flue gas and having a spray dryer vessel inlet duct defined by a duct wall, the apparatus may be used to measure in situ the wet bulb temperature of the flue gas in the dryer vessel inlet duct. A water nozzle and a temperature sensor are both located in the dryer vessel inlet duct. The nozzle sprays water on the sensor and the wet bulb temperature of the flue gas is continuously measured. The apparatus gathers wet bulb temperature data which may be used for process control or for determining whether a leak has occurred within the tubes of a coal-fired steam boiler.

3 Claims, 4 Drawing Sheets

APPARATUS AND METHOD FOR CONTINUOUS MEASUREMENT OF THE WET BULB TEMPERATURE OF A FLUE GAS STREAM

This is a continuation of application Ser. No. 08/148,299 filed Nov. 8, 1993, now abandoned.

BACKGROUND OF THE INVENTION

1. Field of Invention

This invention relates generally to an apparatus for monitoring the wet bulb temperature in flue gas streams. Such monitoring is useful in conjunction with, for example, process control of a spray dryer absorption process and leak detection for boiler tubes within a coal-fired steam boiler.

2. Description of the Related Art

A coal-fired steam boiler produces superheated steam for use in the production of electricity by a turbine generator, and may produce steam for heating or other industrial use.

Two aspects of power generation are relevant background examples for the invention. The first of these aspects concerns detection of leaks in boiler tubes.

A power plant boiler has boiler tubes within which steam is generated. A problem which arises in power plants is leaking boiler cubes. As boiler tubes age through service they may deteriorate and a leak in a boiler tube may develop. When such a leak develops, steam escapes from within the boiler tube into a flue gas duct.

Leaks in boiler tubes result in the loss of thermal performance, and can cause corrosion, deposition, and fouling in downstream equipment. Tube leaks are major causes of power plant unavailability, and can result in a forced outage of the entire boiler system. Small leaks are often undetectable because any loss in performance is usually relatively small. Additionally, these leaks are often concealed by insulation, and are generally inaudible to standard acoustic monitoring equipment. Furthermore, small leaks can become self-compounding and intensify into additional, larger leaks. The water vapor released by these leaks combines with the flue gas impurities to produce acidic, highly corrosive conditions for other boiler tubes and downstream equipment. Measuring the wet bulb temperature within a flue gas duct can provide an indication of whether a boiler tube leak exists since the humidity of flue gas should increase in the event of a leak.

The second relevant background aspect of power generation is discussed in the following paragraphs.

The spray dryer absorption process for removing sulfur dioxide from flue gas utilizes an aqueous slurry of slaked lime (lime mixed with water) to chemically capture sulfur dioxide that is present in the flue gas. The resulting chemical reaction between the slurry and the gas stream leads to the formation of calcium sulfites and sulfates.

The absorber has a dryer vessel in which flue gas is mixed with an atomized slurry of lime ($Ca(OH)_2$) and recycled product (i.e., fly ash, $CaSO_4$, $CaSO_3$, $CaCO_3$, and unreacted $Ca(OH)_2$). This mixing results in droplet drying and simultaneous sulfur dioxide removal yielding a spray dryer waste product consisting of fly ash mixed with calcium-sulfur compounds. Flue gas and most of the waste products then exit the dryer vessel and enter a fabric filter where the waste products are removed. Some of the waste products also drop out of the dryer vessel and are conveyed to a hopper for recycle to the process. Dry waste products collected by the fabric filter may either be recycled or conveyed to disposal. The cleaned flue gas stream which exits the fabric filter is discharged into the ambient air by way of stacks.

To maximize the capture of the sulfur dioxide from the flue gas the "approach to saturation temperature" is controlled. Saturation temperature, or wet bulb temperature, is defined as the lowest temperature at which a given amount of water vapor can be retained before droplets begin to condense. The approach to saturation temperature is defined in the spray drying art as the spray dryer exit temperature minus saturation temperature. Accordingly, both the dry bulb temperature (which is measured in the dryer vessel outlet gas) and the wet bulb temperature (which is measured in the dryer vessel inlet gas) need to be determined. Additionally, these two temperature measurements can be made at several locations both upstream and downstream of the dryer vessel.

For dry scrubbing applications, water vapor contained in the flue gas supplies the driving force for sulfur dioxide removal. The closer the approach to saturation temperature, the greater the removal for sulfur dioxide in the process, and the greater the efficiency of reagent use. Theoretically, the goal in this process would be to achieve identical temperatures for both the wet and dry bulb temperatures. In practice, however, operating in this mode would cause a condition known as "wet bottom" which consists of severe plugging of the spray dryer outlet ductwork due to the saturation by water of the reactive waste product leaving the dryer vessel. Therefore, this key operating parameter for the spray drying process requires that the resulting dry bulb temperature exceed the actual wet bulb temperature by approximately 20 degrees F. In the event that the approach to saturation temperature becomes more than approximately 20 degrees F., then the amount of reagent slurry sent to the spray dryer atomizer is decreased. This decrease in reagent slurry results in less cooling of the flue gas within the spray dryer, and a corresponding higher spray dryer outlet temperature due to a decrease in slurry water content. By measuring both the wet bulb and dry bulb temperatures, the approach to saturation temperature can be controlled through a feedback control loop to the atomizer feed pump supplying the slurry atomizer.

It is occasionally but not commonly a practice for a utility using spray drying technology to measure the wet bulb temperature of the inlet gas. Usually, the dryer vessel outlet gas temperature (dry bulb) will be fixed at a "safe" temperature (145–150 degrees F.) known to be much higher than the calculated saturation temperature. This methodology of control can result in reduced sulfur dioxide removal, and inefficient use of reagent since an unnecessarily large flow of lime reagent slurry is sent to the dryer vessel to insure that the desired level of sulfur dioxide is removed. The net effect is an overall decrease in the amount of system water sent to the dryer vessel. This decrease in system water causes the dryer vessel outlet gas temperature to become unnecessarily higher than that of the wet bulb temperature and thus, artificially raises the approach temperature. Furthermore, the lime reagent used in the spray drying process is costly so this conventional utilization results in increased reagent costs and increased reagent consumption due to the reduced utilization of recycled waste solids.

Attempts have been made to measure the wet bulb temperature in spray dryer systems. For example, a prior art wet bulb measuring apparatus is provided by U.S. Pat. No. 4,809,537, assigned to the assignee of the present invention. The '537 system diverts a sample of flue gas, filters the sample, and reheats the sample to the same temperature as the gas in the flue.

In a unit sensing the wet bulb temperature of a gas stream it is necessary that the surface of the measuring sensor remain wet without becoming clogged with particulates or excessively corroded. Furthermore, the sensor is preferably protected from the corrosive and erosive environments to which it is exposed while maintaining an accurate wet bulb reading. To date, these objectives have proven to be very difficult to attain with a reliable wet bulb temperature measuring instrument.

SUMMARY OF THE INVENTION WITH OBJECTS

It is an object of this invention to provide continuous, real time, wet bulb temperature data for any gas stream.

It is another object of this invention to provide an apparatus for measuring the wet bulb temperature of a flue gas which apparatus is not labor intensive in use.

It is another object of this invention to provide a means for measuring the wet bulb temperature of a flue gas which means is simple in construction and operation compared to the prior art.

It is another object of this invention to provide an apparatus for measuring the wet bulb temperature of a flue gas which apparatus does not require removal of gas from the gas stream.

It is another object of this invention to provide an apparatus for measuring the wet bulb temperature of any gas stream which apparatus allows such measurement at various locations and depths within a duct carrying such flue gas.

It is another object of this invention to provide an improved apparatus for reducing reagent consumption in a sulfur dioxide absorber.

It is another object of this invention to provide an apparatus for measuring the wet bulb temperature of a flue gas which apparatus self cleans its sensor.

It is another object of this invention to provide an improved apparatus for improving the efficiency of sulfur dioxide absorbers.

It is another object of this invention to provide an improved apparatus for leak detection for boiler tubes within a coal-fired steam boiler.

The present invention is a novel wet bulb temperature measuring apparatus which accomplishes these and other objects by featuring the structure that is described below.

In a flue gas scrubber for removing sulfur dioxide from flue gas and having a spray dryer vessel inlet duct defined by a duct wall, the apparatus of the present invention may be used to measure the wet bulb temperature of the flue gas in the dryer vessel inlet duct. The apparatus also may be used to measure gas humidity within a flue gas to indicate whether a boiler tube is leaking in a coal-fired steam boiler. The apparatus has a port through a duct wall which has a support plate removably fixed over the port. The support plate has a first aperture and a second aperture. A first hollow support arm is inserted through the first aperture into the duct. A second hollow support arm is inserted through the second aperture into the duct. A temperature sensor is located within the duct and is fixed to the first support arm. The temperature sensor has sensor leads routed from an exterior location from the inlet duct by way of a hollow interior within the first support arm. A water spray nozzle is located within the duct and is fixed to the second support arm. The water spray nozzle is fed by a water supply line and an atomizing air supply line. The water supply line and the air supply line are routed from an exterior location from the inlet duct by way of the hollow interior of the second support arm. The nozzle sprays water on the sensor and the wet bulb temperature of the flue gas is continuously measured. The apparatus gathers wet bulb temperature data which may be used for process control or for determining whether a leak has occurred within the tubes of a coal-fired steam boiler.

DETAILED DESCRIPTION OF THE PRESENT INVENTION

Figure 1:
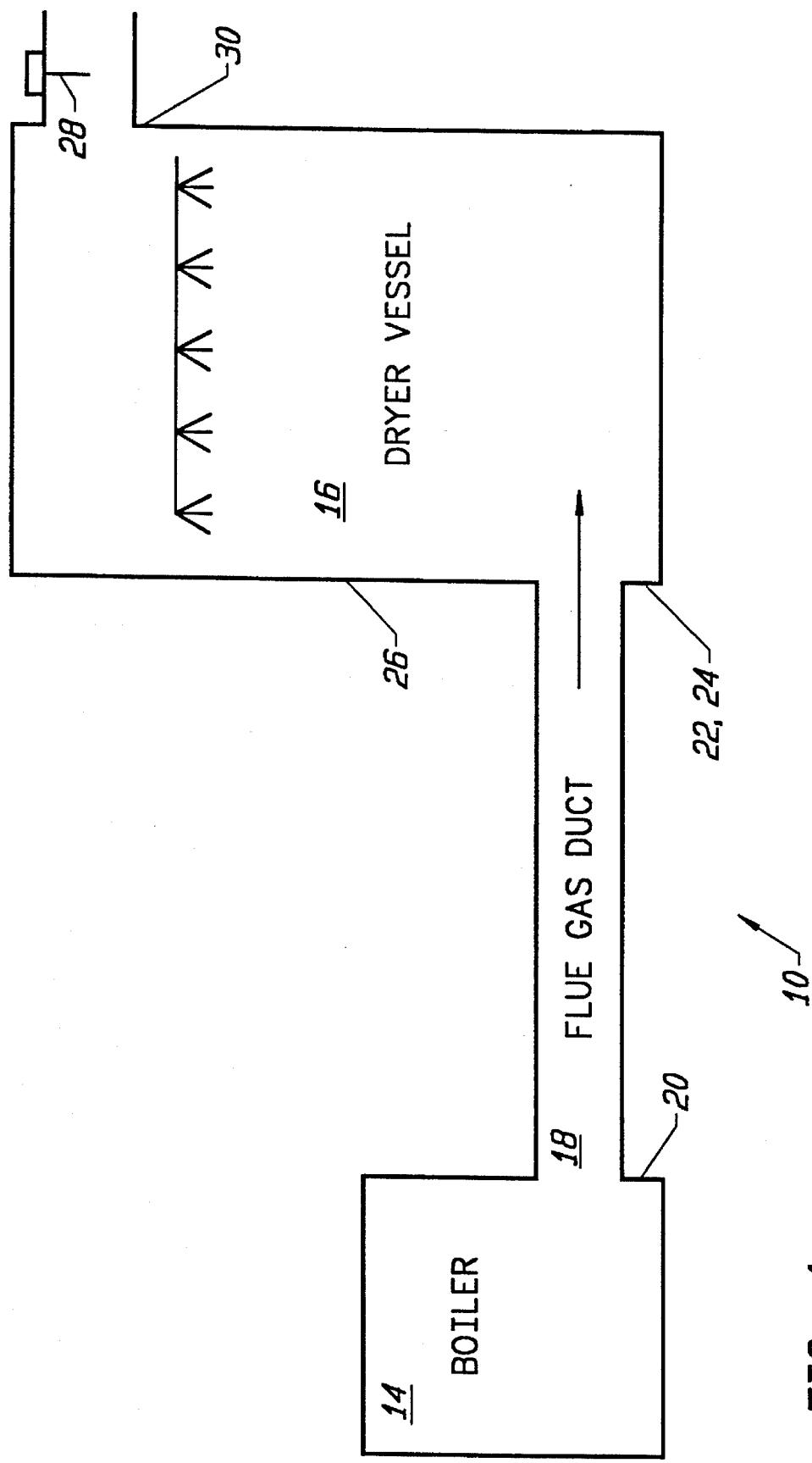
FIG. 1 is a schematic of a conventional power plant with an spray dryer vessel to show the environment in which the present invention is used.

Now referring to FIG. 1, a schematic of a portion of conventional power plant 10 is illustrated in order to show the environment in which the present invention is used. Boiler 14 provides steam for rotating a turbine (not shown). The steam within boiler 14 is heated by combusting coal. Dryer vessel 16 is part of a sulfur dioxide absorber which operates under the principles described in the related art portion of this specification. Combustion of coal produces flue gas which flows from boiler 14 to dryer vessel 16 by way of duct 18 which is a dryer vessel inlet duct. Duct 18 is attached to boiler 14 at duct upstream end 20 and to dryer vessel inlet 22 of dryer vessel 16 at duct downstream end 24. Dryer vessel inlet 22 is an aperture through dryer vessel wall 26 defining dryer vessel 16. Dryer vessel inlet 22 coincides with duct downstream end 24. At duct downstream end 24, duct 18 joins to dryer vessel inlet 22. Accordingly, duct 18 and dryer vessel inlet 22 provide a fluid communication path for flow of flue gas from boiler 14 into dryer vessel 16. The term "downstream" is used to refer herein to a location within duct 18 that is closer to dryer vessel inlet 22 than a specified other location within duct 18. Similarly, the term "upstream" is used herein to refer to a location within duct 18 that is further from dryer vessel inlet 22 than a specified other location within duct 18. Dry bulb thermometer 28 is a conventional thermometer located at the dryer vessel outlet 30.

Figure 2:
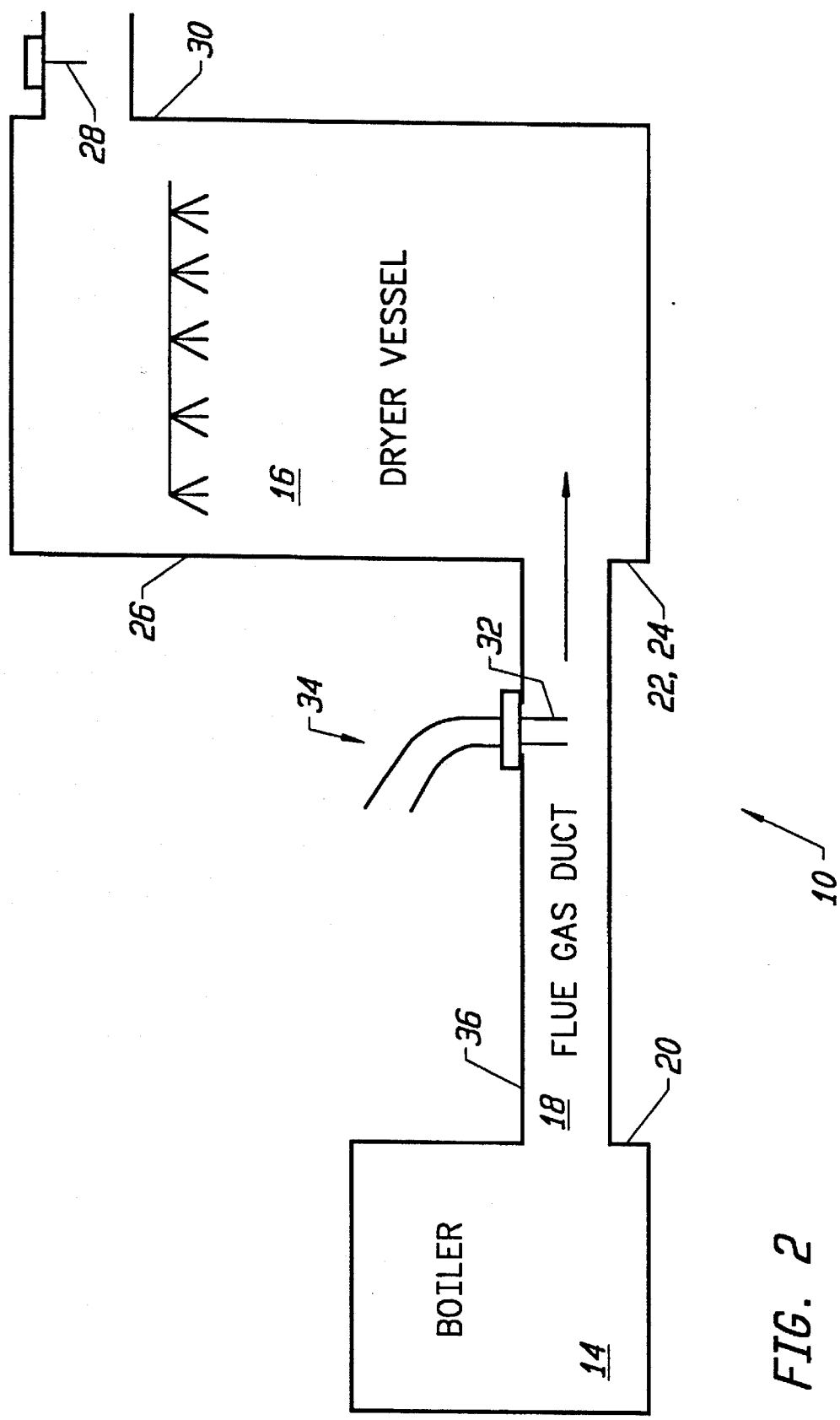
FIG. 2 is a schematic of the power plant and spray dryer vessel of FIG. 1 showing a location that the present invention is installed.

FIG. 2 illustrates a schematic of power plant 10 with dryer vessel 16 of FIG. 1 showing an example location that the present invention is installed. Port 32 is a sealable aperture through duct wall 36. Duct wall 36 is a wall which defines the interior space of duct 18. Port 32 may be pre-existing or may be cut through duct wall 36 specifically for the purposes of installing the present invention. For the purposes of the present invention, port 32 may be located at any location along duct 18 provided that port 32 is upstream of dryer vessel inlet 22. Duct 18 may have runs that are horizontal, vertical, or other orientations and, in accordance with the present invention, port 32 may be located at any of such locations.

While the present invention is described in detail for measuring the wet bulb temperature of a flue gas, the present invention can be used in other environments. It should also be understood that the present invention may be installed in any duct in which hot gas flows. The present invention may similarly be inserted into any gas to be monitored in any sort of environment. However, the present invention is preferably installed in gas streams within locations such as chambers or vessels in which there is a minimum gas flow velocity to evaporate the moisture injected to the sensing apparatus instantaneously. The preferred minimum gas velocity is approximately fifteen feet per second to ensure that heat transfer by convection greatly dominates any transfer by radiation. If radiation is low, the preferred minimum velocity is lowered as well. If gas velocity is not sufficiently high, the temperature to be read will be that of the water temperature not the wet bulb temperature.

Port 32 is sealable to prevent flue gas from escaping duct 18 by way of port 32. Attaching wet bulb temperature measuring apparatus 34 is the usual manner for sealing port 32. If wet bulb temperature measuring apparatus 34 is removed for maintenance, repair, or other purposes, port 32 may be sealed using alternative means, for example, a gasketed plate (not shown) bolted to duct wall 36.

Figure 3:
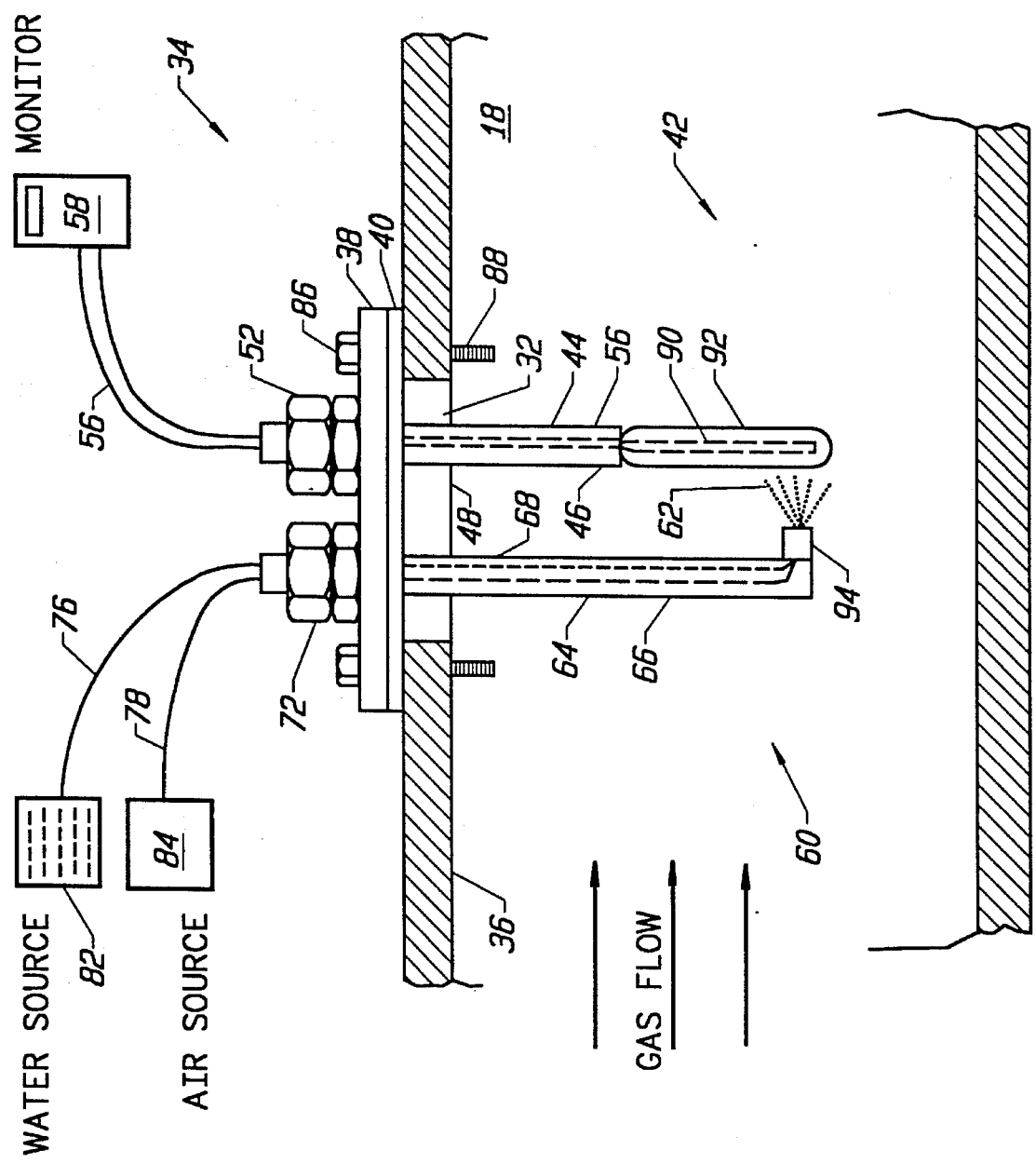
FIG. 3 illustrates a sectional view of the wet bulb temperature measuring apparatus of the present invention.

FIG. 3 shows the wet bulb temperature measuring apparatus 34 of the present invention. Duct 18, sensor support arm 44, and applicator support arm 64 are shown in section to reveal sensor leads and supply lines housed within these support arms. Duct 18 is sealed by disk-shaped support plate 38 and disk-shaped support plate gasket 40. Support plate gasket 40 is sandwiched between support plate 38 and duct wall 36. Sensor 42 is located within the flow of flue gas. Sensor support arm 44 supports sensor 42. Sensor support arm 44 is a tube having a hollow interior sealed from flue gas. Sensor support arm 44 is elongated and has sensor support arm first end 46 and sensor support arm second end 48. Sensor 42 is attached to sensor support arm first end 46. Sensor support arm second end 48 is attached to support plate 38. Sensor support arm 44 is sufficiently rigid as to keep sensor 42 stationary as flue gas flows past sensor 42. Sensor support arm 44 may be oriented perpendicular to support plate 38 or another angle may be selected depending upon which particular location within duct 18 one desires to monitor. Sensor support arm 44 may be elongated to a selectable length to permit monitoring of a particular location within duct 18. For example, as illustrated in FIG. 3, sensor support arm 44 is elongated such that sensor 42 is located in the midst of flue gas flowing through duct 18. Alternatively, sensor support arm 44 may be shortened so that sensor 42 is located closer to or adjacent to support plate 38.

As mentioned above, sensor support arm second end 48 is attached to support plate 38. In the illustrated embodiment, support plate 38 has a sensor insertion aperture (illustrated in FIG. 4) which is an aperture through support plate 38 through which sensor support arm 44 is inserted into the interior of duct 18. Sensor support arm 44 may be held in place by friction provided by sensor compression fitting 52 or may be otherwise removably or permanently fixed to support plate 38.

Sensor support arm 44 is preferably of tubular construction to provide a lead sheath. Sensor leads 56 are preferably shielded from the hostile flue gas environment by housing them within a tubular lead sheath provided by sensor support arm 44 and routing them from sensor 42 to a location exterior from duct 18. Accordingly, a lead sheath is integrated into the structure of sensor support arm 44 as is illustrated. Sensor support arm 44 serves a dual function by both supporting sensor 42 and shielding sensor leads 56 within sensor support arm 44. Support plate 38 has an aperture for permitting sensor leads 56 to pass through support plate 38 to the exterior of duct 18. In the illustrated embodiment, the sensor insertion aperture also serves as the aperture for permitting sensor leads 56 to pass through support plate 38.

Sensor leads 56 are connected to monitor 32. Monitor 32 receives signals from sensor leads 56, processes such signals, and displays them as wet bulb temperature readings. Monitor 32 is a portable, digital continuous temperature monitor which provides a readout of the sensor 42 temperature. A plant operator uses the readings displayed on the monitor 32 to manually or automatically adjust the processes of the dryer vessel 16 in accordance with the objectives set forth in the Description of Related Art portion of this specification.

Water applicator 60 is located within the flow of flue gas. Water applicator 60 sprays water 62 onto sensor 42 thereby making sensor 42 wet. The water 62 spray is water flying in small drops and particles of finely divided water. Applicator 60 imparts a velocity to the drops and particles of water 62 spray. This imparted velocity has a speed and direction such that water 62 is sprayed onto sensor 42. The direction of water 62 velocity as water 62 issues from applicator 60 need not coincide with a straight line between applicator 60 and sensor 42 since rapidly flowing flue gas may add a velocity component to water 62 motion. Applicator support arm 64 is an elongated tube having a hollow interior sealed from the flue gas and has applicator support arm first end 66 and applicator support arm second end 68. Applicator support arm first end 66 supports water applicator 60. Applicator support arm second end 68 is attached to support plate 38. Water applicator 60 is supported by applicator support arm 64 which is sufficiently rigid as to keep water applicator 60 stationary while flue gas flows past water applicator 60. Applicator support arm 64 may be oriented perpendicular to support plate 38 or another angle may be selected depending upon which particular location within duct 18 to which one desires to apply water. Applicator support arm 64 may be elongated to a selectable length. For example, as illustrated in FIG. 3, applicator support arm 64 is elongated such that water applicator 60 is located in the midst of flue gas flowing through duct 18. Alternatively, applicator support arm 64 may be shortened so that water applicator 60 is located closer to or adjacent to support plate 38. The particular orientation and length of applicator support arm 64 are chosen such that water 62 may be applied to sensor 42. In one embodiment of the present invention, sensor support arm 44 and applicator support arm 64 are parallel, approximately of equal length, but separated from each other by about one inch.

As mentioned above, applicator support arm second end 68 is attached to support plate 38. Support plate 38 has applicator insertion aperture (illustrated in FIG. 4) which is an aperture through support plate 38 through which applicator support arm 64 is inserted into duct 18. Applicator support arm 64 may be held in place by friction provided by applicator compression fitting 72 or may be otherwise removably or permanently fixed to support plate 38.

Water supply line 76 supplies water 62 to water applicator 60. Air supply line 78 supplies compressed air to water applicator 60. (An alternative embodiment which does not require air supply line 78 is discussed below.) Applicator support arm 64 is preferably of tubular construction to provide a supply line sheath. Water supply line 76 and air supply line 78 are preferably shielded from the hostile flue gas environment by housing them within a tubular supply line sheath within applicator support arm 64 and routing them from water applicator 60 to a location exterior from duct 18. Accordingly, a supply line sheath is integrated into the structure of applicator support arm 64 as is illustrated in FIG. 3. Tubular applicator support arm 64 serves a dual function by shielding water supply line 76 and air supply line 78 within applicator support arm 64 and thus applicator support arm 64 and supply line sheath are provided by the same tubular structure. Support plate 38 has an aperture for permitting water supply line 76 and air supply line 78 to pass through support plate 38 to the exterior of duct 18. In the illustrated embodiment, applicator insertion aperture 70 also serves as the aperture for permitting water supply line 76 and air supply line 78 to pass through support plate 38. Water supply line 76 is connected to water source 82. Air supply line 78 is connected to air source 84.

In an alternative embodiment of the present invention, applicator support arm 64 may itself be fastened to and supported by sensor support arm 44. The converse is also true that sensor support arm 44 may itself be fastened to and supported by applicator support arm 64. In yet another embodiment, sensor support arm 44 and applicator support arm 64 may be made unitary. That is, a single support member can be used to support both sensor 42 and water applicator 60. Such a single support member would terminate with a two pronged fork, one prong of the fork supporting sensor 42 and the other prong of the fork supporting water applicator 60.

Figure 4:
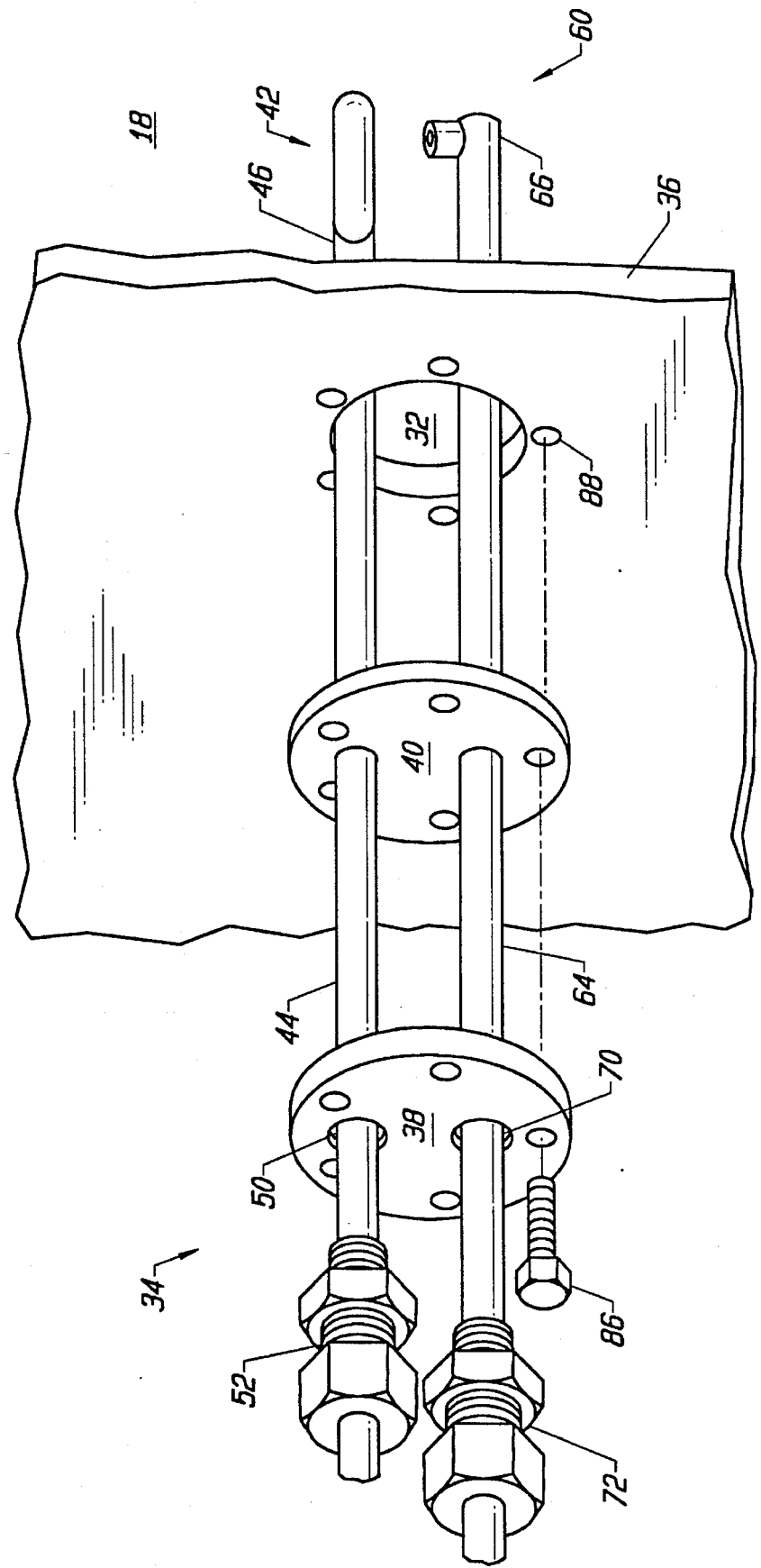
FIG. 4 illustrates an exploded view of a plate and gasket assembly of the present invention.

FIG. 4 illustrates an exploded view of wet bulb temperature measuring apparatus 34 such that one can observe the manner by which it is inserted into duct 18. Wet bulb temperature measuring apparatus 34 is secured to duct wall 36 by bolts 86 which extend through bolt holes 88.

Having generally described wet bulb temperature measuring apparatus 34 of the present invention, a more detailed description of its individual elements is undertaken in the following paragraphs.

Support plate 38 is constructed of stainless steel. The present inventors have found that a distance of one inch separation between sensor 42 and water applicator 60 provides good results. Accordingly, in the embodiment shown in the figures, sensor insertion aperture 50 and applicator insertion aperture 70 are separated from each other by a one inch distance. Support plate 38 may be made with sensor insertion aperture 50 and applicator insertion aperture 70 at varying distances from each other in order to permit optimization of the distance between sensor 42 and water applicator 60. One means for providing sensor insertion aperture 50 and applicator insertion aperture 70 at varying distances is to provide a plurality of support plates 38, each with a different distance between sensor insertion aperture 50 and applicator insertion aperture 70. Alternatively, a single support plate 38 may be provided which has (1) a plurality of sensor insertion apertures 50 along with a single applicator insertion aperture 70; or (2) a plurality of applicator insertion apertures 70 along with a single sensor insertion aperture 50; or (3) a plurality of sensor insertion apertures 50 along with a plurality of applicator insertion apertures 70. When employing one of the three alternatives just enumerated, the sensor insertion apertures 50 and applicator insertion apertures 70 that are not already occupied by either sensor support arm 44 or applicator support arm 64 are sealed to prevent escape of flue gas.

Sensor compression fitting 52 and applicator compression fitting 72 both movably fix sensor support arm 44 and applicator support arm 64 in place and seal flue gas within duct 18. Sensor compression fitting 52 and applicator compression fitting 72 allow convenient movement of sensor 42 and water applicator 60 to various depths within duct 18.

Sensor 42 has a thermocouple 90 exposed from sensor support arm 44. In an embodiment of the present invention that was actually reduced to practice, a six inch length of thermocouple 90 was inserted through sensor compression fitting 52 into support plate 38 and into the gas stream. No sensor support arm 44 was used in this embodiment. The inner six inches of the thermocouple 90 was selected as the sensing region 42 and was coated with Teflon™ sensor coating 92 to protect it from the corrosive environment experienced in that area. In this embodiment, water applicator 60 sprays water 62 along the two inch portion of sensor 42 closest to the tip of sensor 42. Sensor 42 has Teflon™ sensor coating 92. Sensor coating 92 is a layer of material which encloses sensor 42. Sensor coating 92 is applied using Teflon™ heat shrink material. Sensor coating 92 protects thermocouple 90 from corrosion and provides a surface for humidification of thermocouple 90. Alternative means to protect thermocouple 90 could be selected. For example, thermocouple 90 may be surrounded with Polyofin™ tubing. However, the present inventors have found that Polyofin™ material is not as temperature resistant as Teflon™ material. Another example of a protective covering for thermocouple 90 is to construct the thermocouple 90 itself out of Hastelloy-C™ material.

In the embodiment actually reduced to practice, thermocouple 90 is a standard 18"×¼" 316 L stainless steel grounded thermocouple of the type J or K. Alternatively, a resistance thermal detector ("RTD") may be used in place of a thermocouple. In an alternative embodiment of the present invention, thermocouple 90 is grounded. A grounded thermocouple has one lead welded to the protective sheath. Grounded thermocouple 90 provides a faster response than non-grounded thermocouple 90.

Sensor support arm 44 is constructed of Hastelloy™ material. This material is resistant to both erosion and corrosion. It should be appreciated that as water 62 is introduced into the acidic flue gas stream, the gas condenses and forms an aerosol of liquid and gaseous acid. Unless corrosion resistant material is used for sensor support arm 44, the acid will damage sensor support arm 44. The temperature of water 62 does not appear to affect the wet bulb temperature measured because water 62 is heated by the hot flue gas as it travels to nozzle 94. The water may be heated or cooled, depending upon its temperature at the exit of nozzle 94 may be heated much higher than the wet bulb temperature if the flue gas is cool enough to allow the water spray to reach the wet bulb temperature.

Water applicator 60 is constructed of Hastelloy™ material. Water applicator 60 has swirling air atomizing nozzle 94 which provides the constant measured humidification that sensor 42 requires. Nozzle 94 produces a conical-shaped spray of atomized water 62 to humidify the end of sensor 42 where the wet bulb reading will occur. Alternatively, nozzle 94 may be selected to deliver a fan-shaped spray pattern of water 62 rather than a conical one.

A further alternative for water applicator 60 is to employ a nozzle 94 that does not require atomizing air. Atomization of water 62 without air would make the system structurally simpler. However, an obstacle to this approach is that a non-atomizing nozzle 94 would be flow-specific, that is, the flow and pressure of the atomized water 62 stream would be fixed for each particular nozzle 94. Any desired change in this set flow would require a substitution of nozzle 94. With the air atomizing nozzle 94, the present invention can deliver many different water 62 flows using the same nozzle 94.

The preferred location of water applicator 60 places water applicator 60 upstream from sensor 42. It is also preferred that nozzle 94 be located and aimed at sensor 42 such that water 62 is sprayed in a direction that is the same direction as flue gas flow. This upstream location permits water 62 to readily wet sensor 42. After having wetted sensor 42 then water 62, wetted ash, and overspray are carried away from sensor 42 by flue gas. Placement of water applicator 60 upstream from sensor 42 also avoids the necessity higher speed of spray velocities that would be needed to spray against the flow of flue gas. It should be noted that this orientation of water applicator 60 also provides a self-cleaning function for sensor 42 since water 62 washes away ash particulates that would otherwise accumulate on sensor 42. The upstream location of water applicator 60 prevents ash particulates that have been washed away from sensor 42 from returning in the direction of water applicator 60.

Applicator support arm 64 is constructed of stainless steel. It may be noted that applicator support arm 64 is not wetted and therefore not as exposed to the corrosive attack seen by sensor 42 and sensor support arm 44.

Water supply line 76 is constructed of a Teflon™ tube. Other tube materials could be selected. Such other materials are preferably corrosion resistant and flexible for ease in routing from water source 82 to water applicator 60. Water supply line 76 may be fitted with an excess flow check valve in order to eliminate excess quantities of water from being injected into the ductwork in the event of leaks in the water supply line 76 or in nozzle 94.

Several options are available for outputting collected data. A connection may be made to a temperature readout device for manual data collection. A connection may be made to a recorder or data acquisition system for automatic data collection and trending. Finally, a connection may be made to a computerized process controller for automatic control of process conditions based on instrument output.

In one embodiment, the apparatus is inserted into a boiler flue gas duct defined by a duct wall. the apparatus measures flue gas humidity to indicate whether a leak has occurred within the tubes of a coal-fired steam boiler. The percentage of water vapor in the flue gas is reflected by the saturation (or wet bulb) temperature of the flue gas. Thus, the measured value of the wet bulb temperature of a flue gas can be an indicator of the amount of water added to the gas by leaking steam tubes. When compared to a benchmark wet bulb temperature (defined as the wet bulb temperature without leaking tubes), the measured temperature can be used to calculate the amount of steam (or water vapor) added to the flue gas by a leak. This in turn provides an indication as to whether the tube leak is characterized as small, marginal, or large. With this type of wet bulb temperature monitor in place, boiler tube leaks can be detected, and repairs scheduled, at the beginning of a leak rather than by experiencing a forced outage after the leak becomes too large to maintain normal power plant operation.

TEST RESULTS

The present invention was tested in a pilot plant operated by the assignee of the present invention. The pilot plant is a research facility for emission control technologies for coal-fired utility power plants that burn high-sulfur coals. The pilot plant consists of a 4-MWe wet scrubbing flue gas desulfurization system, a 0.4-MWe wet scrubbing flue gas desulfurization system, and a 4-MWe dry scrubbing flue gas desulfurization system.

At the pilot plant, the effects of periodic measurement of the wet bulb temperature have been studied and measured. The tested embodiment used a Teflon™ material for sensor coating 92.

The performance of the tested embodiment was recorded and tracked as it was simultaneously operated and compared to wet bulb measurements that were manually taken. The manually taken measurements were taken using a conventional psychrometric method involving inserting into a duct a thermocouple that is wetted by a wick in contact with the thermocouple.

An example of test results of the present invention shows its close agreement with the manually obtained results. The difference between the results shows there to be a very small error of the invention. This data reflects a highly accurate and reliable apparatus, and was repeatedly achieved throughout similarly tests with the invention.

Four instantaneous measurements were taken over a two hour period with both the present invention and manually. The results of this test was as follows:

| Comparison of Wet Bulb Temperature Measurements (Degrees Fahrenheit) | | |
|---|---|---|
| Time | Present Invention | Manual Measurement |
| 12:55 | 124 | 123.8 |
| 13:10 | 124 | 123.6 |
| 14:05 | 124.2 | 125 |
| 14:45 | 124.4 | 125.2 |

The temperature measurement obtained with the present invention was 292 degrees prior to activation of the water supply of the present invention. This 292 degree temperature was the dry bulb temperature of the flue gas. Within approximately five minutes after the water supply was activated, the temperature reading dropped to 124 degrees to provide the wet bulb temperature. Similarly, once the water supply was deactivated, the temperature reading outputted by the present invention rose to the dry bulb temperature within approximately five minutes. This example illustrates the response of the invention to changing conditions within the flue gas duct.

In one test series of the present invention, the present invention was removed from duct 18 thirty hours later. A small build-up of soft ash had accumulated on sensor 42 approximately two inches from the tip of sensor 42. The self-cleaning effect of the present invention was demonstrated by the absence of particulate accumulation on the wetted portion of sensor 42.

The temperature of water 62 does not significantly affect the measurements of the wet bulb temperature due to heating or cooling of water 62 by flue gas. This heating or cooling occurs both as water 62 passes through water supply line 76 and as water 76 moves from water applicator 60 to sensor 42.

Water 62 used to wet sensor 42 does not affect the absorption process of dryer vessel 16. A large amount of water 62 introduced into the process could affect the reagent-to-water ratio and affect sulfur dioxide removal efficiency. At the very low water 62 flow rates used in the pilot-scale process test (gas flows of 8000–12000 scfm), the introduction of water 62 is barely noticeable and affects the flue gas humidity by less than one percent. At full scale utility application, the impact of water 62 introduced should be even less.

The invention provides benefits over the prior art since the present invention has no moving parts. This reduces the system complexity, reduces the need for maintenance, and increases reliability. The invention does not require reservoirs for samples and does not require heaters. Similarly, the invention does not require filters, wicks, or sampling assemblies which are high maintenance parts that typically require periodic cleaning and replacement. Moreover, the present invention is not labor intensive since the present invention can operate without a person attending it.

The invention provides benefits since it provides in situ measurement of actual duct conditions. Previously used extractive systems require substantial conditioning of the gas sample to approximate the conditions within the gas duct.

The invention uses common, commercially available parts and materials for ease of service, repair, and availability for spare or replacement parts and materials. Materials are selected for corrosion and erosion resistance to the elements within the flue gas.

The flange mounted to the gas duct allows quick and easy removal of the entire apparatus. This provides trouble-free and timely inspection, repair, and replacement.

The lengths, distances, angles, selected materials of construction, nozzle types, measurement locations, and other design factors disclosed herein are representative. Persons skilled in the art of the present invention may, upon exposure to the teachings herein, conceive other variations. Such variations are deemed to be encompassed by the disclosure, the invention being limited only by appended claims.

We claim:

1. In a flue gas scrubber for removing sulfur dioxide from flue gas and having a dryer vessel inlet duct defined by a duct wall, an apparatus for measuring the wet bulb temperature of said flue gas in a dryer vessel inlet duct, said apparatus comprising:

a port through said duct wall;

a support plate removably fixed to said duct wall over said port, said support plate having a first aperture and a second aperture;

a first support arm inserted through said first aperture into said inlet duct, said first support arm having a hollow interior sealed from said flue gas;

a temperature sensor located within said inlet duct and fixed to said first support arm, said temperature sensor comprised of a thermocouple having a protective coating, said temperature sensor having sensor leads routed from said temperature sensor to an exterior location from said inlet duct by way of said hollow interior of said first support arm;

a second support arm inserted through said second aperture into said inlet duct, said second support arm having a hollow interior sealed from said flue gas;

a water spray nozzle located within said inlet duct and fixed to said second support arm, said water spray nozzle aimed to spray water onto said temperature sensor;

a water supply line to supply water to said water spray nozzle, said water supply line routed from said water spray nozzle to an exterior location from said inlet duct by way of said hollow interior of said second support arm; and an air supply line to supply atomizing air to said water spray nozzle, said air supply line routed from said water spray nozzle to an exterior location from said inlet duct by way of said hollow interior of said second support arm.

2. An apparatus for measuring the wet bulb temperature of a gas within a duct, said apparatus comprising:

a first support arm inserted into said gas;

a temperature sensor located on said first support arm;

a first compression fitting to movably fix said first support arm such that said temperature sensor may be moved to different depths within said duct;

a second support arm inserted into said gas;

a water spray nozzle located on said second support arm, said water spray nozzle aimed to spray water onto said temperature sensor; and a second compression fitting to movably fix said second support arm such that said water spray nozzle may be moved to different depths within said duct.

3. The apparatus of claim 2 wherein said temperature sensor has a coating to protect said temperature sensor from damage caused by said flue gas.

* * * * *